United States Patent
Erkamp et al.

(10) Patent No.: US 11,064,969 B2
(45) Date of Patent: Jul. 20, 2021

(54) AUTOMATIC CONFIGURATION DETECTION FOR SENSOR EQUIPPED NEEDLE

(71) Applicant: KONINKLIJKE PHILIPS N.V., Eindhoven (NL)

(72) Inventors: Ramon Quido Erkamp, Swampscott, MA (US); Ameet Kumar Jain, Boston, MA (US); Francois Guy Gerard Marie Vignon, Croton on Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 491 days.

(21) Appl. No.: 15/301,786

(22) PCT Filed: Apr. 2, 2015

(86) PCT No.: PCT/IB2015/052424
§ 371 (c)(1),
(2) Date: Oct. 4, 2016

(87) PCT Pub. No.: WO2015/155644
PCT Pub. Date: Oct. 15, 2015

(65) Prior Publication Data
US 2017/0209116 A1 Jul. 27, 2017

Related U.S. Application Data
(60) Provisional application No. 61/978,196, filed on Apr. 11, 2014.

(51) Int. Cl.
*A61B 8/00* (2006.01)
*A61B 8/08* (2006.01)
(Continued)

(52) U.S. Cl.
CPC .......... *A61B 8/0841* (2013.01); *A61B 8/4438* (2013.01); *A61B 8/585* (2013.01); *A61B 90/92* (2016.02); *A61B 90/96* (2016.02)

(58) Field of Classification Search
None
See application file for complete search history.

(56) References Cited

U.S. PATENT DOCUMENTS

| | | | |
|---|---|---|---|
| 4,697,595 A | 10/1987 | Breyer | |
| 5,720,293 A * | 2/1998 | Quinn | A61B 5/028 600/505 |

(Continued)

FOREIGN PATENT DOCUMENTS

| | | |
|---|---|---|
| EP | 2424440 B1 | 1/2014 |
| JP | 10099327 A | 4/1998 |

(Continued)

OTHER PUBLICATIONS

Barr, Richard G. "Improved Needle Visualization with Electronic Beam Steering", Ultrasound Quarterly, vol. 28, No. 2, Jun. 2012.

(Continued)

*Primary Examiner* — Joel F Brutus

(57) ABSTRACT

A system for automatic configuration detection includes a medical device (250) including a sensor (246). A pattern (236) is coded into a portion of the medical device. The pattern is configured to store pertinent information about the device. A reader device (234) is coupled to a connector and configured to read the pattern to convey the pertinent information to determine one of a status, identity or manner of use for the medical device including the sensor.

20 Claims, 3 Drawing Sheets

(51) Int. Cl.
  *A61B 90/96* (2016.01)
  *A61B 90/92* (2016.01)

(56) References Cited

U.S. PATENT DOCUMENTS

| | | | |
|---|---|---|---|
| 5,872,455 A | 2/1999 | Pohribnij | |
| 2004/0171935 A1 | 9/2004 | Van Creveld | |
| 2004/0230116 A1* | 11/2004 | Cowan | A61B 17/2202 |
| | | | 600/437 |
| 2007/0156125 A1* | 7/2007 | DeLonzor | A61B 10/0233 |
| | | | 606/21 |
| 2008/0140006 A1* | 6/2008 | Eskuri | A61B 5/00 |
| | | | 604/117 |
| 2009/0128330 A1* | 5/2009 | Monroe | A61B 50/30 |
| | | | 340/568.1 |
| 2009/0326369 A1* | 12/2009 | Schmidt | A61B 5/06 |
| | | | 600/424 |
| 2010/0168562 A1* | 7/2010 | Zhao | A61B 34/30 |
| | | | 600/426 |
| 2012/0143029 A1 | 6/2012 | Silverstein | |
| 2013/0041252 A1* | 2/2013 | Vignon | A61B 8/0841 |
| | | | 600/424 |
| 2013/0041258 A1* | 2/2013 | Patrick | A61B 8/00 |
| | | | 600/439 |
| 2013/0211221 A1 | 8/2013 | Sunnarborg et al. | |
| 2014/0031674 A1* | 1/2014 | Newman | A61B 8/0833 |
| | | | 600/424 |

FOREIGN PATENT DOCUMENTS

| | | |
|---|---|---|
| JP | H1099327 A | 4/1998 |
| JP | 2013106789 A | 6/2013 |
| RU | 2413465 C1 | 3/2011 |
| WO | 2007047404 A2 | 4/2007 |

OTHER PUBLICATIONS

Nichols, Kremer et al "Changes in Ultrasonographic Echogenicity and Visibility of Needles with Changes in Angles of Insonation", J Vasc Interv Radiology, vol. 14, No. 12, 2003.

Cheung, Stephanie et al "Enhancement of needle visibility in ultrasound-guided percutaneous procedures", Ultrasound in Medicine & Biology, vol. 30, Issue 5, May 2004—Abstract Only.

* cited by examiner

AUTOMATIC CONFIGURATION DETECTION FOR SENSOR EQUIPPED NEEDLE

CROSS-REFERENCE TO PRIOR APPLICATIONS

This application is the U.S. National Phase application under 35 U.S.C. § 371 of International Application No. PCT/IB2015/052424, filed on Apr. 2, 2015, which claims the benefit of U.S. Provisional Patent Application No. 61/978,196, filed on Apr. 11, 2014. These applications are hereby incorporated by reference herein.

RELATED APPLICATION INFORMATION

This application claims priority to U.S. provisional application Ser. No. 61/978,196, filed on Apr. 11, 2014, incorporated herein by reference in its entirety.

BACKGROUND

Technical Field

This disclosure relates to medical instruments and more particularly to a system and method to track a tip of a needle (or other device) where the needle and sensor arrangement are conveyed using an optical code.

Description of the Related Art

In ultrasound imaging, the visibility of the needle is often very poor due to the specular nature of the needle surface that reflects beams away from the imaging probe. To alleviate this problem some needle manufacturers have produced needles with special echogenic coatings, but the visualization improvement is limited. Ultrasound imaging system manufacturers have developed algorithms that use multiple imaging beams from varied angles, but improvement is limited and such a strategy is primarily suited only for linear arrays. Both strategies do not help when the needle is inserted perpendicular to the imaging plane or the needle path has a small offset relative to the imaging plane.

One solution that has been proposed to visualize the tip of interventional tools such as needles, but also catheters, is to add ultrasound receivers near the tip of the tool. While the imaging beam sweeps the field of view, the signals from the sensors indicate how close the beams are getting to the sensor. This information is used to calculate sensor position relative to the ultrasound image with positional accuracy exceeding 0.5 mm, even under conditions where the needle is not visible in the ultrasound image. The sensor needs to not interfere with the functionality of the device (e.g., not block the lumen, not interfere with the mechanics, e.g., for an automatic biopsy device, etc.).

To obtain the orientation of the needle, multiple sensors are needed. To obtain the location of the tip, the distance between these sensors and the tip needs to be known to the imaging system. The number of sensors and their relative locations to the tip are parameters that will change depending on what needle is used for the procedure. Other hardware parameters, such as sensor acoustic calibration results (including impulse response, sensitivity and acceptance angle) may also be needed in specific algorithms.

SUMMARY

In accordance with the present principles, a system for automatic configuration detection includes a medical device having a sensor. A pattern is coded into a portion of the medical device. The pattern is configured to store pertinent information about the device. A reader device is coupled to a connector and configured to read the pattern to convey the pertinent information to determine one of a status, identity or manner of use for the medical device including the sensor.

Another system for automatic configuration detection includes a needle having an ultrasound sensor disposed thereon. A connector is configured to couple the ultrasound sensor to an ultrasound imaging device. A pattern is coded into a portion of the needle, and the pattern is configured to store pertinent information about the needle. A reader device is coupled to the connector and configured to read the pattern to convey the pertinent information to the imaging device, the pertinent information including one of a status, identity or manner of use of the needle and/or the sensor.

A method for automatic configuration detection includes applying a pattern coded into a portion of a medical device, the pattern configured to store pertinent information about the device, the medical device including an ultrasound sensor; reading the pattern by a reader device coupled to a connector, which connects to the sensor, to convey the pertinent information to an imaging device to determine one of a status, identity or manner of use for the medical device and/or the sensor; and triggering an alert or action based upon the pertinent information.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
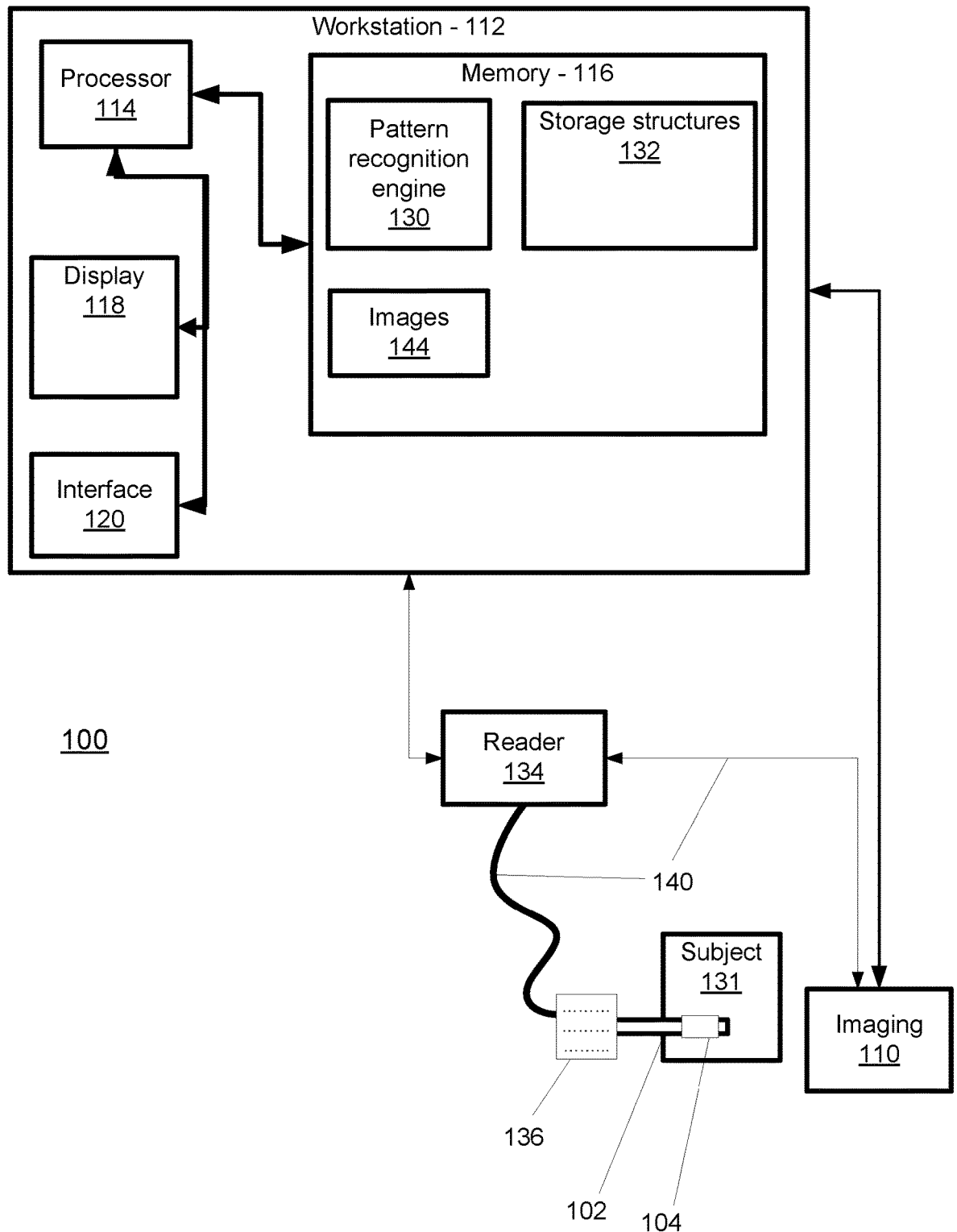
FIG. 1 is a block/flow diagram of an automatic configuration detection system in accordance with the present principles.

In accordance with the present principles, systems, devices and methods are provided for conveying device parameters to a tracking system in an easy and efficient manner. To accurately determine and visualize a position of a tip of a medical instrument, an imaging system needs to know specific hardware parameters. For example, the position of tracking sensors relative to the tip needs to be known. The present principles provide an automatic mechanism for transferring such information from the needle or other device to the imaging system without the need for additional actions from the user. This minimizes negative impact on the workflow.

In one embodiment, a machine readable pattern is provided that includes relevant information on a hub of the needle or on an equivalent location on a different device. This pattern is then detected by an appropriate sensor integrated in a needle connector that connects the needle sensors to the imaging system. The information may include a model number, a position vector, an electronic file name or address, etc. that the imaging system can use to reference a device specification, lookup table or a series of numbers that indicate exact sensor distances from a device tip and other parameters, such as, e.g., receiver calibration results.

The present principles reduce workflow obstacles and also minimize workflow changes due to employing the device. In addition, medical reporting can be streamlined by automatically annotating images with device specific information. Further, through device serial number tracking, accidental reuse of disposable devices and use of expired devices that may have compromised sterility can be prevented.

Some needle devices such as standard biopsy needles are low cost but high volume disposables. It is desirable to put an optical pattern on a hub of the device. For example, a standard biopsy needle has a rectangular plastic hub with 7 mm×10 mm sides. A pattern could be directly deposited on that face, or a sticker with the pattern could be attached to such a location. The pattern could be picked up with a low cost miniature CCD sensor such as, for example, CCD sensors employed in smartphones (e.g., 4.5×3.4 mm, 8 Mpix). In one embodiment, the CCD sensor is brought in direct contact with the pattern, and a light emitting diode (LED) source may be employed for back lighting. With a 600 dot per inch (dpi) pattern, this gives up to 8500 bits of information. This is more than adequate to employ with a redundant error correcting coding scheme for added robustness (for example, Reed-Solomon (RS) error correcting code, used in compact disks, 2D bar codes, space transmission, etc.). Alternative embodiments may include, for example, a conductive ink pattern and contact pad array type sensor, color coding with a color sensor, shape/geometry based device markings, etc.

It should be understood that the present invention will be described in terms of medical instruments; however, the teachings of the present invention are much broader and are applicable to any instrument that can accept an optical code. In some embodiments, the present principles are employed in tracking or analyzing complex biological or mechanical systems. In particular, the present principles are applicable to internal tracking procedures of biological systems and are applicable for procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

As one having ordinary skill in the art will appreciate in view of the teachings provided herein, features, elements, components, etc. described in the present disclosure/specification and/or depicted in the Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a system 100 for reading and processing coded information from a medical device is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a pattern recognition engine 130 or other application configured to interpret patterns associated with a medical device 102. Memory 116 may also store one or more storage structures 132, such as, e.g., look up tables, electronic files, etc. The medical device or instrument 102 may include a needle, catheter, a guidewire, a probe, an endoscope, a robot, an electrode, a filter device, a balloon device or other medical component.

Workstation 112 may be coupled to a reader 134 for reading a pattern 136 on the device 102. The reader 134 may include an optical scanner, optical sensor, bar code reader (1D or 2D), or other input device depending on a form of the pattern 136. The reader 134 preferably reads the pattern 136 wirelessly.

An imaging system 110 is coupled to the workstation 112 (or the workstation 112 may be integrated into the imaging system 110, or vice versa). The imaging system 110 may include an ultrasound system, although the imaging system 110 may include other imaging modalities, e.g., computed tomography (CT), fluoroscopy, magnetic resonance, etc. In one embodiment, the medical instruments or device 102 is guided during a procedure using images from the imaging device 110. Prior to connecting the device 102 to workstation 112 or to imaging device 110, the pattern 136 is read by the reader 134 and interpreted by the pattern recognition engine 130. The recognized pattern 136 may provide pertinent data regarding the device 102 or provide a memory location (e.g., in structures 132) where pertinent data is stored regarding the device 102.

The pertinent data of the coded pattern 136 for the device 102 may include, e.g., information about or for determining a needle tip location, e.g., needle length, gauge, sensor position, or other geometry information that is specific to the needle device that is being tracked. The pertinent data of the coded pattern 136 may include other sensor/device geometry, acoustic calibration (for ultrasound imaging systems), expiration date, serial number, etc. In other embodiments, the pertinent data of the pattern 136 may include stored use information, e.g., a disposable device may have its serial number or other information logged into the data structure 132 and, prior to use, the serial number is checked to determine whether the device 102 has been used previously (previously logged in). The pertinent data may be transferred to the workstation 112 and/or the imaging system 110 so that the pertinent data may be provided in images, employed to provide a warning or communicate other information to a user.

In one embodiment, the reader 134 is included on a connector 140 (e.g., a connecting cable or wire) used to connect to the device 102 (to send or receive signals to/from the device 102, provide power to the device 102. In one embodiment, the device 102 includes a needle having an ultrasound transducer 104 integrated thereon. The transducer power and input/output signals may be carried using the connector 140. The connector to the needle device 102 with the embedded sensor/transducer 104 may include the reader 130 for detecting the pattern 136. Since the connector 140 already connects to the imaging system 110 (and/or the workstation 112), the connector 140 provides a method for transferring the information in the pattern 136 to the imaging system 110 (or workstation 112).

The transfer of information to imaging system 110 may be provided by the connector 140 that is attached to the device 102 that conveys information from its embedded sensor 104 to the imaging system 110. A physical cable may be employed, e.g., a standard universal serial bus (USB) connection with a camera, miniature webcam assembly, etc. Alternatively, the connector 140 may include a small rechargeable battery and transmit the information wirelessly (e.g., a small wireless camera). A Bluetooth® based communication channel may be employed.

The device type/model information may be used to put the imaging system 110 in a preconfigured mode that is appropriate for the type of procedure that the particular device 102 is commonly used for. Alternatively, the imaging system 110 may keep track of imaging settings of past procedures performed with that device type/model, and pre-configure imaging settings based on historical usage of the device 102.

Workstation 112 includes a display 118 for viewing internal images of a subject (patient) or volume 131. The display 118 can display an image 144 of the volume 131 or display an overlay image over another rendering of the volume 131. Display 118 may also permit a user to interact with the workstation 112 and its components and functions, imaging device 110, or any other element within the system 100. This is further facilitated by an interface 120, which may include a keyboard, mouse, a joystick, a haptic device, or any other peripheral or control.

Figure 2:
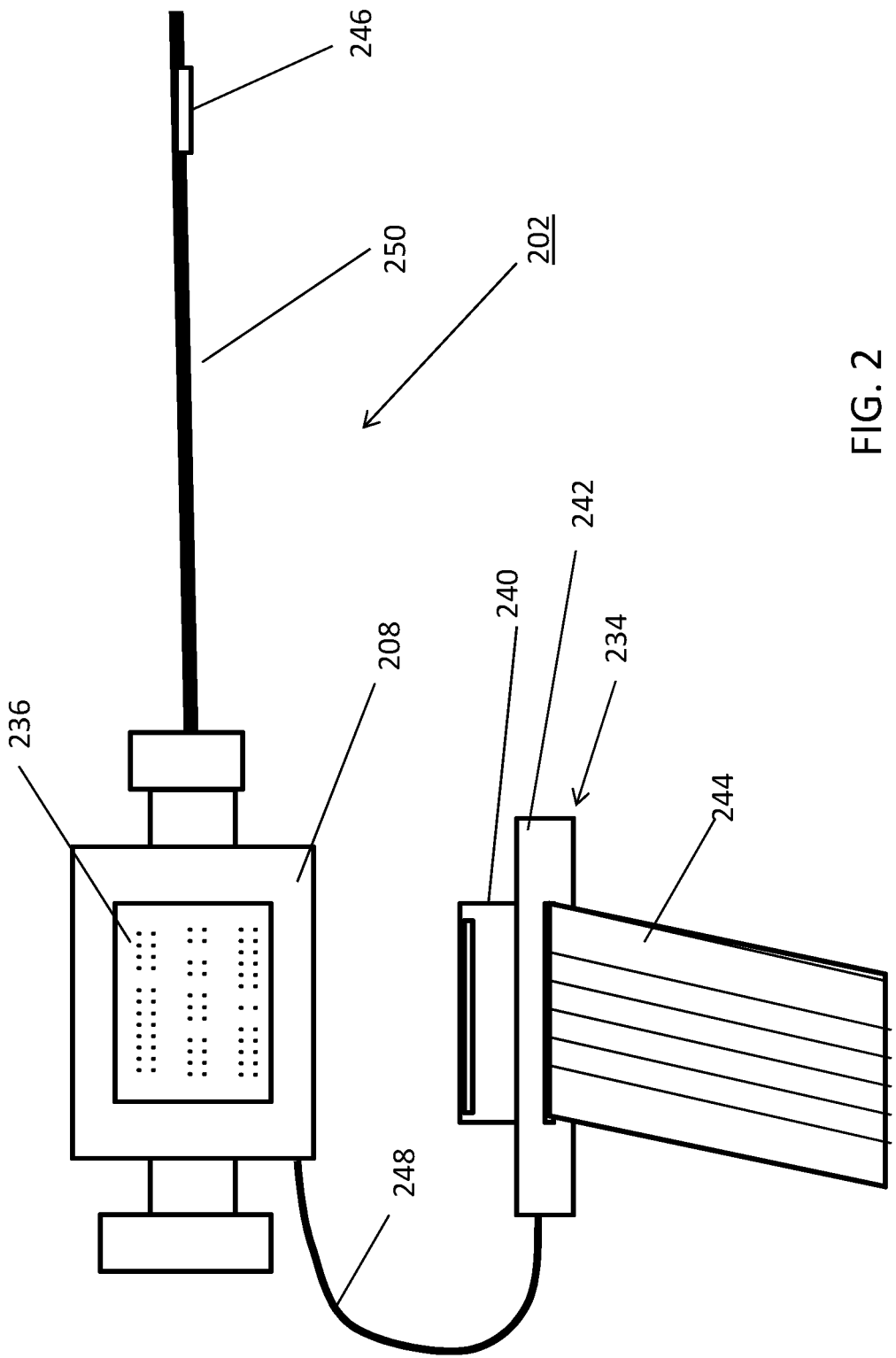
FIG. 2 is a diagram showing a needle having a pattern code displayed thereon and a reader for reading the pattern in accordance with illustrative embodiments.

Referring to FIG. 2, an exemplary embodiment shows a coded pattern 236 on a needle device 202 in accordance with one embodiment. While the pattern 236 is illustratively depicted as a 2D bar code or dot pattern, there are many ways to physically apply a pattern to the needle device 202. The optical pattern 236 may be applied to a flat surface of a needle hub 208, e.g., by applying a small sticker or other coating as the method of application.

Instead of an optical pattern, a pattern (236) of electrically conductive ink may be employed. This electrically conductive pattern may be scanned optically using reflected light or electrically using electrical charge or current flow (e.g., a coil or other circuit component). In another embodiment, a pattern may be formed by changing the geometry of the device, e.g., by adding an array of small pits of varying sizes or attaching a small key-like structure, etc. These may also be read using a photodiode or laser (e.g., similar to compact disk readers). In another embodiment, a color coding scheme may be employed. For example, a color code may be read that follows a scheme similar to what is employed for indicating a magnitude for electrical resistors. Colors may represent standard sizes, shapes or other characteristics of the device 202. The colors and their relative positions may be read using a reader 234 (e.g., a camera or other type of sensor). In this case, the reader 234 includes a CCD camera 240 mounted on a substrate 242 (e.g., printed circuit board, etc.). The camera 240 may be a part of a cable or connector 244 (e.g., ribbon cable) that connects to a workstation or an imaging device. The camera 240 may be part of or connect to a device, such as a smart phone or other handheld pattern reading device. In one embodiment, an ultrasound sensor 246 mounted on a needle 250 (or other medical instrument) may be connected to the reader 234 by a cable 248.

The coded pattern 236 may be configured to hold a sufficient amount of information to encode all sensor locations relative to a tip of the needle 202, acoustical calibration results, and additional information such as device type/model, serial number, and expiration date. In this way, the imaging system (110, FIG. 1) does not need to rely on a lookup table that needs to be updated to visualize the position of the tip when new devices become available. The device type/model information may be used to put the imaging system (110, FIG. 1) in a preconfigured mode that is appropriate for the type of procedure that the particular needle device 202 is commonly used for. Alternatively, the imaging system may keep track of imaging settings of past procedures performed with that device type/model, and pre-configure imaging settings based on historical usage of the device 202.

The serial number can be used to detect if a disposable device is accidentally reused. In addition, serial number tracking can be used to initiate automatic restocking requests or to enforce certain device usage policies (batch of needles can only be used within certain hospital to prevent reselling or theft). The expiration date information can be used to ensure sterility of the devices. If receiver/transducer calibration data are included in the pattern (either through direct encoding or by reference to a lookup table), one could verify if the device 202 is still performing similarly to when it left the factory or if some degradation of performance has taken place. The calibration data may include acoustic performance under well-defined conditions but also may include non-acoustic parameters, e.g., sensor capacitance or resistance, noise behavior in absence of an ultrasound signal, etc. The degradation could be either due to storage conditions of the needles or due to a malfunction in the electronics of the particular ultrasound system being used.

It may be desirable to have a coded pattern 236 with significant redundancy. This permits the use of robust error correcting encoding. For example, Reed-Solomon (RS) coding can be very robust even in the presence of long sequences of corrupted data, and is used in applications ranging from CD data storage to deep space communications, and in 2D bar code readers.

While the location for the pattern 236 may be on the needle hub 208, a pattern may be placed on the needle itself, instead of or in addition to, the needle hub 208. This may be appropriate if in the manufacturing process of the sensor equipped needle, the equipment that is employed to deposit materials on the needle can also apply the coded pattern (near the hub end) or on the needle itself.

An embedded sensor or camera 240 for pattern readout may be implemented in a plurality of ways. For example, the implementation of the readout sensor 240 depends on the type of pattern. In one embodiment, a 2D optical bar code reader or a CCD camera sensor may be used for reader or sensor 240. Such sensors are mass produced, have very high performance, are very small and are very inexpensive. For example, the camera sensor (240) employed in a smartphone may be employed, which has an active area of, e.g., about 4.5 mm by 3.4 mm and 5 MPixels. This sensor 240 could be brought into direct contact with the optical pattern 236, while providing an LED based backlighting from the opposite side (not shown) of the needle hub 208 (e.g., for a translucent or partially translucent hub 208). If the optical pattern 236 is, e.g., applied at a modest 600 dpi black and white printing resolution, this provides about 8500 bits of information. This is more than enough to encode all relevant device parameters with a very high degree of redundancy.

The transfer of information to the imaging system may be provided by a CCD camera 240 which connects to the connector 244. The connector 244 also transfers signals to/from the device 202 (through cable 248) that conveys information from its embedded sensor (US sensor or transducer) to the imaging system. In one embodiment, a physical cable(s) 244, 248 may be employed, although wireless connects may also be employed.

If an electrically conductive pattern is used, an array of contact electrodes (based on, for example, zebra connectors with conductive silicone composites) could be used for readout by direct contact with the pattern 236 (which may include electrically conductive ink or the like). Geometry encoded information could be read out either through optical means (camera) or by mechanical contact sensing methods.

The present principles may be employed for any medical device including but not limited to needles, for example, any instrument insertable into a body and, in particular, under ultrasound guidance. This includes needle procedures (e.g., biopsies, ablation, anesthesia, pain management, abscess drainage, etc.) and catheter procedures (e.g., heart repair, electrophysiology, etc.). In the case of flexible catheters, a sensor (close to the tip) or a multitude of sensors (along the catheter) may be employed. For a catheter, it may be useful to encode the mechanical flexibility limitations of the device in the pattern to aid shape fitting of the device to the detected sensor locations.

Figure 3:
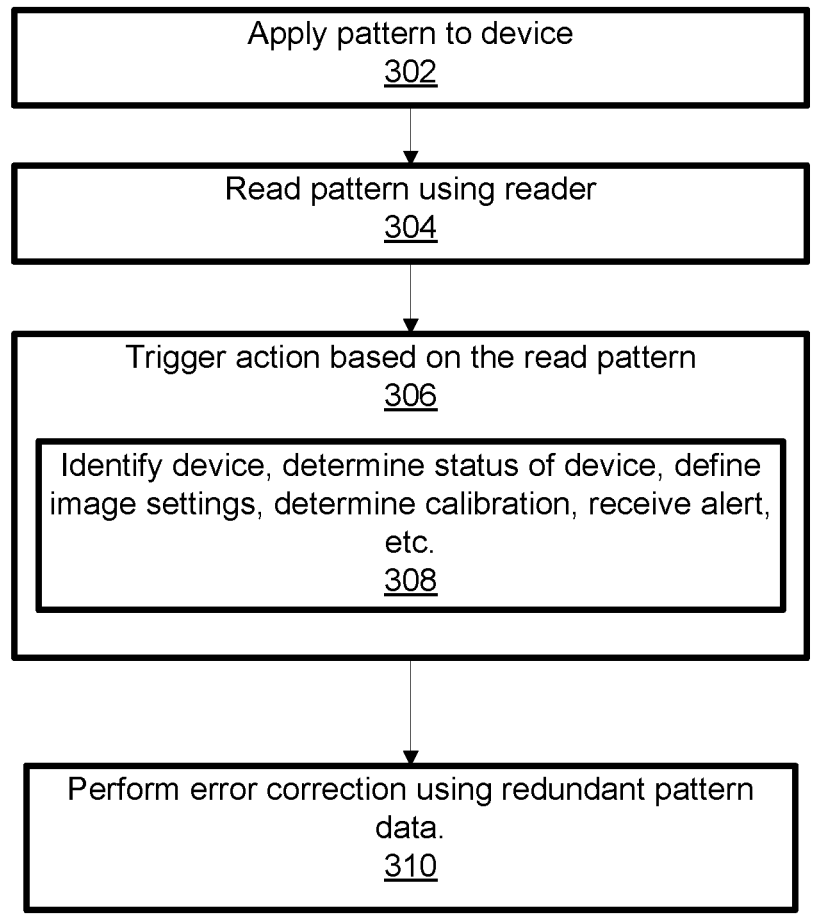
FIG. 3 is a flow diagram showing a method for automatic configuration detection in accordance with illustrative embodiments.

Referring to FIG. 3, a method for automatic configuration detection is illustratively shown. In block 302, a pattern or code is applied onto a portion of a medical device. The pattern is configured to store pertinent information about the device. The medical device includes a sensor or other device. For example, the sensor may include an ultrasound sensor. The medical device may include, e.g., a needle (or catheter) and the portion of the medical device where the pattern is located may include a hub, on a shaft of the needle or any other convenient location(s) on the device.

In block 304, the pattern is read by a reader device coupled to a connector. The connector connects the sensor to an imaging device (and/or a workstation) to convey the pertinent information to an imaging device to determine one of a status, identity or manner of use for the medical device and/or the sensor. Reading the pattern may include one or more of reading the pattern with a camera or scanner, and the pattern includes a bar code; reading the pattern with a camera, and the pattern includes a color coding scheme;

reading the pattern with electrical leads, and the pattern includes an electrically conductive material contactable by the electrical leads; or reading the pattern with an optical sensor or a mechanical probe, and the pattern includes mechanical features. Other reading methods and pattern types are also contemplated.

The status, identity or manner of use for the medical device may include one or more of a type of device, a serial number of the device, a geometric configuration of the device, an expiration date of the device, an imaging mode to use with the device or calibration data for the sensor. Other parameters may be stored for the medical device as well.

In block 306, an alert or action is triggered based upon the pertinent information. In block 308, at least one of reuse information for the device, image settings for the device, calibration data associated with the device, etc. may be stored in a data structure. Upon identifying the device, an alert or action is triggered. For example, an alert that the device has been used already or is expired may be conveyed to a user on a display. In another example, a request to restock that model or serial number device may be triggered. Imaging settings or an imaging mode may be set for the imaging device based on the model or configuration of the device as conveyed by the pattern. Calibration information may be stored and compared to determine if the device is properly calibrated or the calibration has changed. Other alerts or actions are also contemplated.

In block 310, the pattern may include redundant data for error code correction configured to provide error correction of the pattern, e.g., RS code or the like.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for automatic configuration detection for a sensor equipped needle (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for automatic configuration detection, comprising:
an insertable medical instrument including an ultrasound sensor for tracking the insertable medical instrument;
a pattern coded into a portion of the insertable medical instrument, the pattern configured to store calibration information the for the insertable medical instrument and the ultrasound sensor; and
a reader circuit coupled to a connector and configured to read the pattern to determine from the calibration information at least one of a noise of the ultrasound sensor in absence of an ultrasound signal, a capacitance of the ultrasound sensor, or a resistance of the ultrasound sensor.

2. The system as recited in claim 1, wherein the connector connects the ultrasound sensor to an ultrasound imaging device.

3. The system as recited in claim 1, wherein the reader circuit includes a camera or scanner and the pattern includes a bar code.

4. The system as recited in claim 1, wherein the reader circuit includes a camera and the pattern includes a color coding scheme.

5. The system as recited in claim 1, wherein the reader circuit includes electrical leads and the pattern includes an electrically conductive material contactable by the electrical leads.

6. The system as recited in claim 1, wherein the pattern includes mechanical features and the reader circuit includes an optical sensor or a mechanical probe.

7. The system as recited in claim 1, wherein the insertable medical instrument includes a needle and the portion of the insertable medical instrument is located on a hub or on a shaft of the needle.

8. The system as recited in claim 1, wherein the calibration information include at least one of a status and an identity of the insertable medical instrument, and wherein the one of the status and the identity of the insertable medical instrument includes at least one of: a type of the insertable medical instrument, a serial number of the insertable medical instrument, a geometric configuration of the insertable medical instrument, imaging mode to use with the insertable medical instrument and calibration data for the ultrasound sensor.

9. The system as recited in claim 1, further comprising a memory that stores at least one of: image settings for the insertable medical instrument, and calibration data associated with the medical device to trigger at least one of an alert and an action upon identifying the insertable medical instrument.

10. The system as recited in claim 1, wherein the pattern includes redundant data for error code correction.

11. A system for automatic configuration detection, comprising:
a needle having an ultrasound sensor disposed thereon;
a connector that couples the ultrasound sensor to an ultrasound imaging device;
a pattern coded into a portion of the needle, the pattern configured to store calibration information for the needle and the ultrasound sensor; and
a reader circuit coupled to the connector and configured to read the pattern to convey the calibration information to the ultrasound imaging device to determine from the calibration information at least one of a noise of the ultrasound sensor in absence of an ultrasound signal, a capacitance of the ultrasound sensor, or a resistance of the ultrasound sensor.

12. The system as recited in claim 11, wherein the reader circuit includes one of: a camera or scanner when the pattern includes a bar code; a camera when the pattern includes a color coding scheme; electrical leads when the pattern includes an electrically conductive material contactable by the electrical leads; or one of an optical sensor or a mechanical probe when the pattern includes mechanical features.

13. The system as recited in claim 11, wherein the pattern is located on a hub or on a shaft of the needle.

14. The system as recited in claim 11, wherein the calibration information includes at least one of a status and identity of the needle, and wherein the at least one of the status and the identity includes at least one of: a type of needle, a serial number of the needle, a geometric configuration of the needle, imaging mode to use with the needle, and calibration data for the ultrasound sensor.

15. The system as recited in claim 11, further comprising a memory that stores at least one of: image settings for the needle, and calibration data associated with the needle to trigger at least one of an alert and an action upon identifying the needle.

16. The system as recited in claim 11, wherein the pattern includes redundant data for error code correction.

17. A method for automatic configuration detection, comprising:
   applying a pattern coded into a portion of an insertable medical instrument, the insertable medical instrument including an ultrasound sensor for tracking the insertable medical instrument, wherein the pattern is configured to store calibration information for the insertable medical instrument and the ultrasound sensor;
   reading the pattern by a reader circuit coupled to a connector that connects to the ultrasound sensor, to determine from the calibration information at least one of a noise of the ultrasound sensor in absence of an ultrasound signal, a capacitance of the ultrasound sensor, or a resistance of the ultrasound sensor; and
   triggering at least one of an alert and an action based upon the calibration information.

18. The method as recited in claim 17, comprising:
   reading the pattern with a camera or scanner when the pattern includes a bar code;
   reading the pattern with a camera when the pattern includes a color coding scheme;
   reading the pattern with electrical leads when the pattern includes an electrically conductive material contactable by the electrical leads; or
   reading the pattern with an optical sensor or a mechanical probe when the pattern includes mechanical features.

19. The method as recited in claim 17, wherein the calibration information includes at least one of a status and identity of the insertable medical instrument, and wherein the one of the status and the identity includes at least one of: a type of the insertable medical instrument, a serial number of the insertable medical instrument, a geometric configuration of the insertable medical instrument, imaging mode to use with the insertable medical instrument, and calibration data for the ultrasound sensor.

20. The method as recited in claim 17, further comprising storing at least one of: image settings for the insertable medical instrument, and calibration data associated with the insertable medical instrument to trigger the at least one of the alert and the action upon identifying the insertable medical instrument.

* * * * *